US00PP21425P2

(12) United States Plant Patent
Madsen

(10) Patent No.: US PP21,425 P2
(45) Date of Patent: Oct. 26, 2010

(54) ***RHIPSALIDOPSIS* PLANT NAMED 'PKMRH02'**

(50) Latin Name: *Rhipsalidopsis×hybrida*
Varietal Denomination: PKMRH02

(75) Inventor: Christian Hald Madsen, Korsor (DK)

(73) Assignee: Gartneriet PKM A/A, Odense N (DK)

( * ) Notice: Subject to any disclaimer, the term of this patent is extended or adjusted under 35 U.S.C. 154(b) by 0 days.

(21) Appl. No.: 12/455,167

(22) Filed: May 29, 2009

(51) Int. Cl.
*A01H 5/00* (2006.01)

(52) U.S. Cl. ..... Plt./372

(58) Field of Classification Search ..... Plt./372
See application file for complete search history.

*Primary Examiner*—Susan B McCormick Ewoldt
(74) *Attorney, Agent, or Firm*—Foley & Lardner LLP

(57) ABSTRACT

A new and distinct *Rhipsalidopsis* plant named 'PKMRH02' particularly characterized by its large upright to vertical flowers which are red-purple in color; buds in red-purple color; freely branching growth habit; and ovoid to lanceolatoid in shape buds.

4 Drawing Sheets

Latin name of the genus and species of the plant claimed: *Rhipsalidopsis×hybrida.*

Variety denomination: 'PKMRH02'.

BACKGROUND OF THE INVENTION

The present invention relates to a new and distinct cultivar of *Rhipsalidopsis* plant, botanically known as *Rhipsalidopsis×hybrida* sometimes referred to as *Rhipsalidopsis* Britton Et Rose, including *Epiphylopsis* Berger, commonly known as either Easter Cactus or Spring Cactus, and hereinafter referred to by the cultivar name 'PKMRH02'.

The new *Rhipsalidopsis* cultivar is a product of a controlled breeding program conducted by the inventor, Christian Hald Madsen, in Søhus, Denmark. The objective of the breeding program was to develop a new *Rhipsalidopsis* cultivar with compact, freely branching habit and unique colored flowers.

The new *Rhipsalidopsis* cultivar originated from a cross made by the inventor in 2005 in Søhus, Denmark. The female and male parents are unpatented, proprietary *Rhipsalidopsis× hybrida* pollinated cultivars. The new *Rhipsalidopsis* cultivar was discovered and selected by the inventor as a single flowering plant within the progeny of the stated cross in a controlled environment in 2007 in Søhus, Denmark. The inventor selected 'PKMRH02' on the basis of its bud and flower color, upright, plant habit and freely branching habit.

Asexual reproduction of the new *Rhipsalidopsis* cultivar by phylloclade cuttings was first performed May of 2007 in Søhus, Denmark, and has demonstrated that the combination of characteristics as herein disclosed for the new cultivar are firmly fixed and retained through successive generations of asexual reproduction. The new cultivar reproduces true to type.

BRIEF DESCRIPTION OF THE INVENTION

The following traits have been repeatedly observed and are determined to be unique characteristics of 'PKMRH02' which are combination distinguish this *Rhipsalidopsis* as a new and distinct cultivar:

1. Large upright to vertical flowers which are red-purple in color;
2. Buds in red-purple color 3. Freely branching growth habit; and
4. Ovoid to lanceolatoid in shape buds.

Plants of the instant cultivar 'PKMRH02' differ primarily from plants of the parental cultivars primarily in bud color. Plants of 'PKMRH02' have red-purple colored buds whereas plants of the parental cultivars have red colored buds.

The most similar commercial cultivar to the instant cultivar 'PKMRH02' is *Rhipsalidopsis* 'SCORPIUS' (patented, EU Grant no. 20676). Plants of the instant cultivar 'PKMRH02' differ primarily from plants of *Rhipsalidopsis* 'SCORPIUS' in the following characteristic:

1. Plants of 'PKMRH02' have bi-colored flowers which are red, closest to RHS 43C and red-purple, closest to RHS 74B, whereas plants of *Rhipsalidopsis* 'SCORPIUS' have one-colored flowers, closest to RHS 53C;
2. Plants of 'PKMRH02' have green phylloclades (closest to RHS 137C) whereas plants of *Rhipsalidopsis* 'SCORPIUS' have darker green phylloclades (closest to RHS 137A); and
3. Plants of 'PKMRH02' have bi-colored sepals (closest to RHS 45A and RHS 178B) whereas plants of *Rhipsalidopsis* 'SCORPIUS' have one-colored sepals (closest to RHS 53A).

BRIEF DESCRIPTION OF THE PHOTOGRAPHS

The accompanying photographs illustrate the overall appearance of the new *Rhipsalidopsis* cultivar 'PKMRH02' showing the colors as true as is reasonably possible with colored reproductions of this type. Colors in the photographs may differ slightly from the color values cited in the detailed botanical description, which accurately describe the color of 'PKMRH02'.

'PKMRH02'

DETAILED BOTANICAL DESCRIPTION

Figure 1:
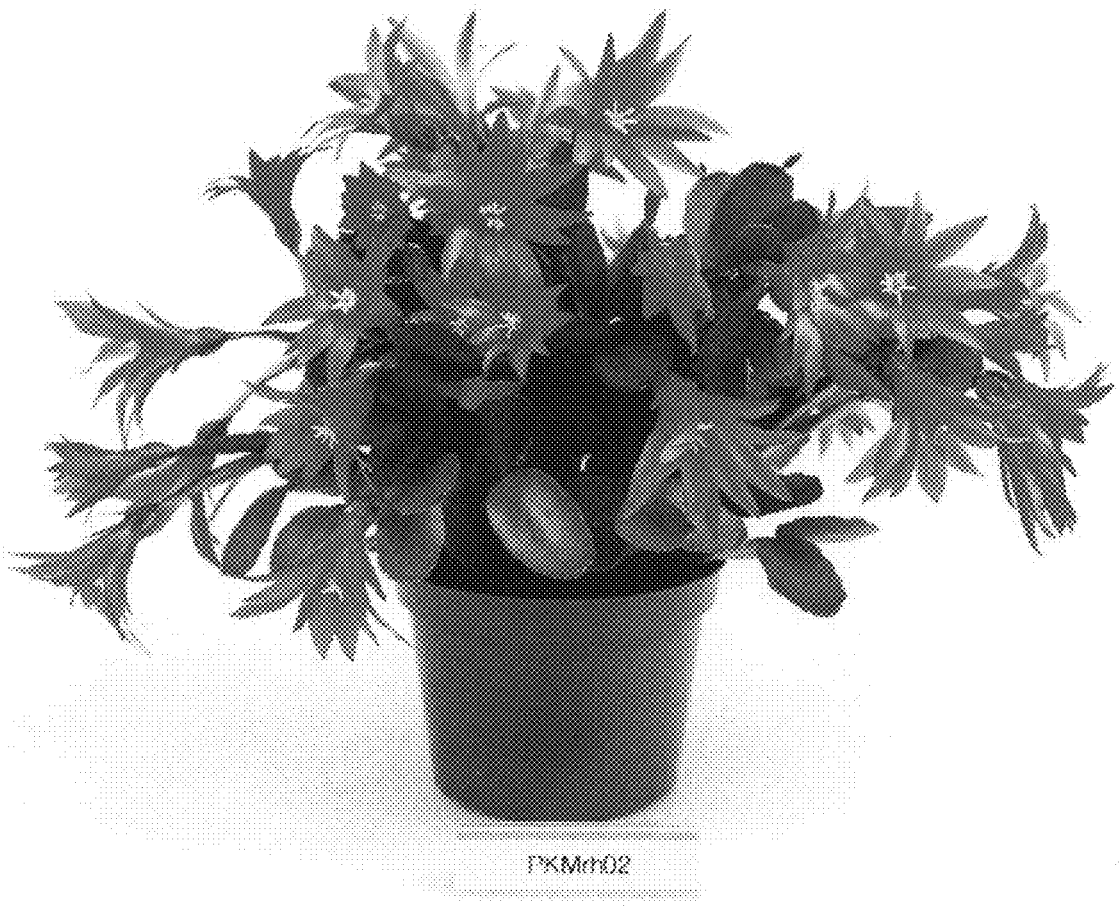
FIG. 1 shows a side perspective view of a typical flowering plant of 'PKMRH02' grown in a 9.0 cm pots, at about 12 months of age.
Figure 2:
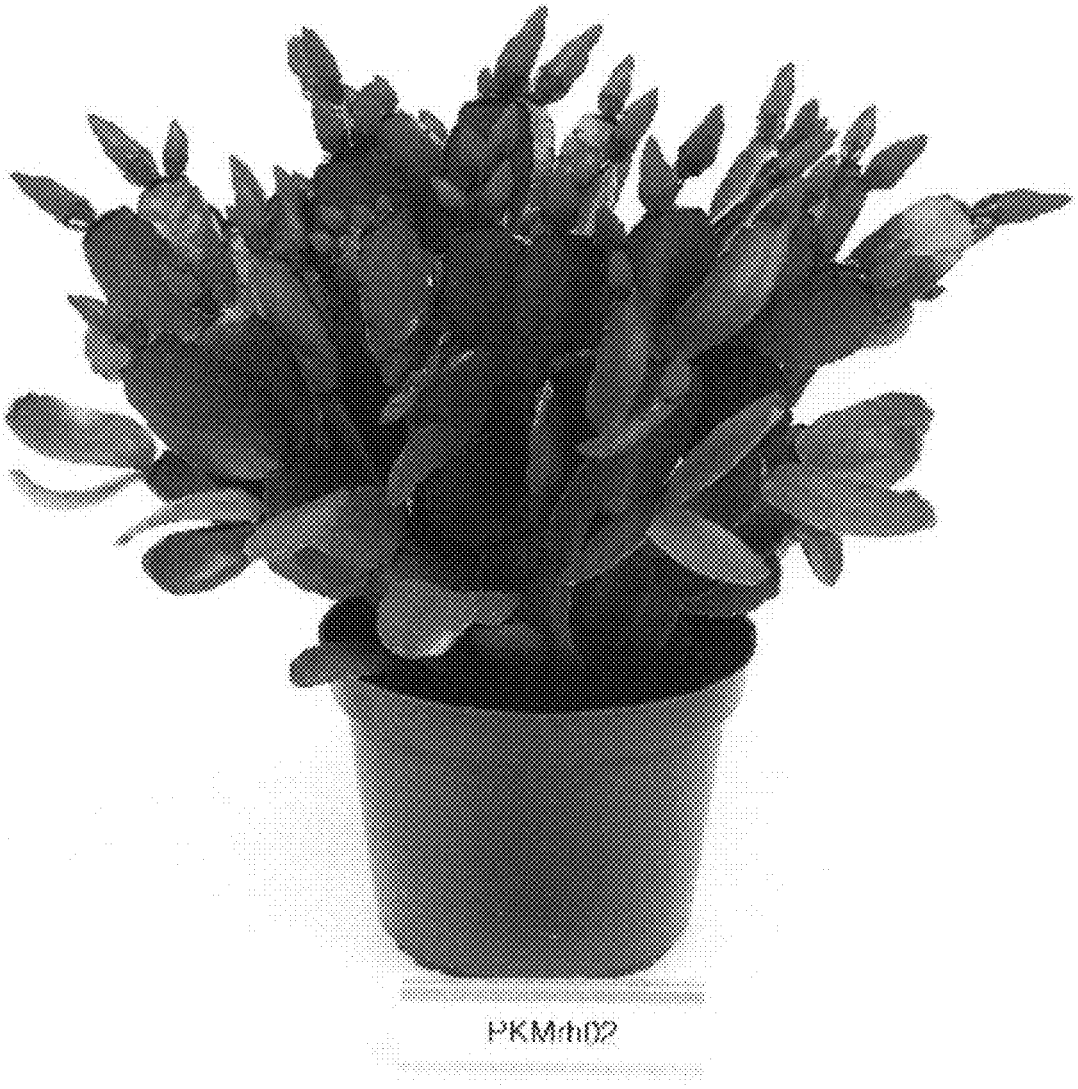
FIG. 2 shows a side perspective view of a typical plant of 'PKMRH02' with buds before opening, as grown in a 9.0 cm pots, at about 12 months of age.
Figure 3:
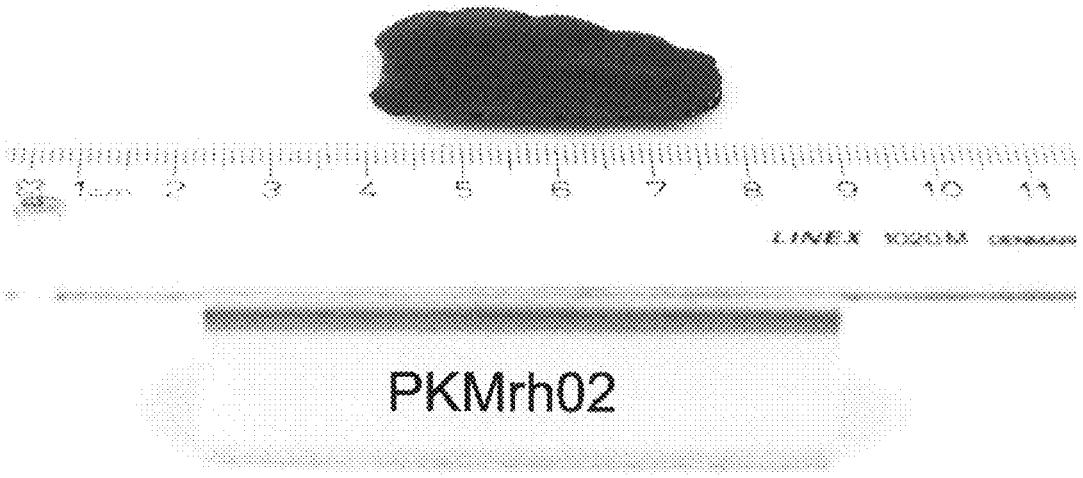
FIG. 3 shows a close-up view of a typical phylloclade of 'PKMRH02' at about 12 months of age.
Figure 4:
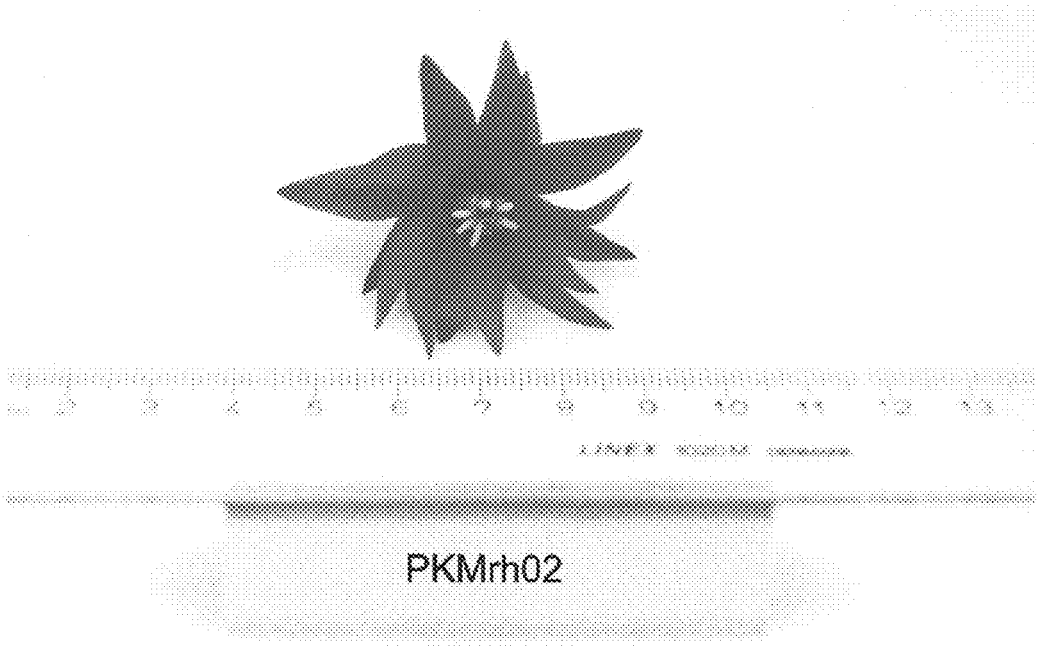
FIG. 4 shows a close-up view of a typical mature flower produced by 'PKMRH02' at about 12 months of age.

The new *Rhipsalidopsis* cultivar 'PKMRH02' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe plants of 'PKMRH02' as grown in a glass-covered greenhouse in Fyn, Denmark, under conditions which closely approximate those generally used in commercial practice, where day temperatures in the greenhouse average 18° C. and night temperatures in the greenhouse average 16° C. Ambient light levels used while growing plants of 'PKMRH02' bare +50 $Wm^2$. Plants of 'PKMRH02' are thermo-photo-periodic and will develop buds and bloom best day after short day treatments for 6 to 8 weeks and cool day/night temperatures of about 8° C. No growth retardants were used when growing plants of 'PKMRH02'.

The age of the 'PKMRH02' plants described is 12 months old and grown in 9.0 cm pots. The photographs and descriptions were taken during the winter season. Color references are made to The Royal Horticultural Society Colour Chart (R.H.S.), $4^{th}$ edition, except where general colors of ordinary significance are used.

Classification:

*Botanical.*—*Rhipsalidopsis* Britton Et Rose.

*Common name.*—Easter Cactus or Spring Cactus.

Parentage:

*Female or seed parent.*—Unpatented, proprietary *Rhipsalidopsis* Britton Et Rose cultivar.

*Male or pollen parent.*—Unpatented, proprietary *Rhipsalidopsis* Britton Et Rose cultivar.

Propagation: By phylloclade cuttings.

*Time and temperature to initiate roots.*—In a greenhouse, about 30 days at 18° C. to 21° C.

*Time and temperature to produce a rooted young plant.*—In a greenhouse, about 60 days at at 18° C. to 21° C.

*Rooting habit and description.*—Fine, well-branched and red-purple, RHS N74B, in color.

Plant:

*Type.*—Perennial, Epiphyte.

*Growth habit.*—Initially erect and upright, becoming pendent as lateral branches lengthen.

*Branching habit.*—Freely branching, with two or three new phylloclades forming at the apical end of older phylloclades.

*Vigor.*—Slow growth rate.

*Crop time.*—After rooting, about 11 months are required to produce a finished flowering plant in an 9 cm pot.

*Size at maturity.*—Height (soil level to top of plant, including flowers): About 15 cm. Spread: About 18 cm to 20 cm.

Stem: None, older phylloclades may turn woody with age (several years).

Lateral branches:

*Arrangement.*—Phylloclades form at the apex of older phylloclades to form branches.

*Quantity.*—About 9 to 12, when 3 phylloclade cuttings planted per pot.

*Length.*—Primary: About 3 cm to 5 cm (1 phylloclade). Secondary: About 12 cm (3 or 4 phylloclades).

*Width.*—About 2 cm to 3 cm.

*Aspect.*—Upright to arching (from basal phylloclade).

*Strength.*—Strong (from basal phylloclade).

*Appearance.*—Dull/matte.

*Pubescence.*—None.

Phylloclade:

*Arrangement.*—Single and sequential.

*Length.*—About 3 cm to 4 cm.

*Width.*—About 1.5 cm to 2.5 cm.

*Thickness.*—About 1 mm to 3 mm (at center vein of phylloclade).

*Overall shape.*—Oval.

*Apex shape.*—Truncate.

*Base shape.*—Rounded.

*Margin.*—Crenate.

*Texture.*—Glabrous, smooth.

*Pubescence.*—None.

*Color of immature phylloclade.*—Upper and lower surfaces: RHS 137C, green.

*Color of mature phylloclade.*—Upper and lower surfaces: RHS 137A, green.

*Venation.*—Pattern: Costate. Color: Upper and lower surfaces: RHS 137C, green.

Areole: Not true areole structure; tip of phylloclade is barbellate, 5 to 12 short hairs or bristles.

Inflorescence description:

*Arrangement and appearance.*—Single, double or triple sessile flowers born on apical end of phylloclades. Flowers are tubular, hose-in-hose perianth. When flowers are fully open, they form a right angle to the phylloclade. Flowers persistent.

*Natural flowering season.*—Flowering occurs from February to April (northern hemisphere), but can be changed depending on short day photo-treatments.

*Flowering response time.*—About 8 to 9 weeks after short day and vernalization.

*Rate of flowers opening.*—About 2 per week, depending on temperature and light.

*Flowering longevity* (*dependent on temperature and light conditions*).—About 5 to 6 days.

*Fragrance.*—None.

*Quantity of flowers per lateral branch.*—About 1 to 3.

*Quantity of buds per lateral branch.*—About 2.

*Quantity of flowers and buds per plant.*—About 30 to 45.

*Flower bud.*—Length: Ranging from 0 to 25 mm (before anthesis). Width: Ranging from 0 to 1 cm. Shape: Ovoid to lanceolatoid. Color: RHS 60C, red-purple.

*Flower.*—Type: Single. Shape: Tubular, hose-in-hose triple perianth. Aspect: Upright to vertical during development. Persistent or self-cleaning: Persistent.

*Corolla size.*—Height: About 3.5 cm to 4.5 cm (including ovary). Diameter: About 3 cm to 5 cm. Tube length: About 2 cm to 3 cm. Tube diameter: About 10 mm.

*Petals.*—Quantity: Apical Whorl: About 10; Basal whorl: About 5 to 7. Length: About 1.5 cm to 3.5 cm. Width: About 6 mm to 8 mm. Shape: Oval. Apex: Retuse Base: Apical Whorl: Fused; Basal Whorl: Free. Margin: Entire. Appearance: Matte. Texture: Silky. Color (When Opening): Upper and lower surfaces: Petals: RHS 74B, red-purple. Tube: Center stripe/tube: RHS 43C, red. Color (When Fully Opened): Upper and lower surfaces: Petals: RHS 74B, red-purple. Tube: Center stripe/tube: RHS 43C, red. Color Fades to: RHS 61A, red-purple.

*Petaloids.*—Arrangement: Free. Quantity: About 3 to 4. Length: About 10 mm to 12 mm. Width: About 5 mm to 7 mm. Shape: Oval. Apex: Acute. Base: Fused. Margin: Entire. Texture (both surfaces): Silky. Color (mature and immature): RHS 46A, red.

*Sepals.*—Quantity: About 3. Length: About 3 mm to 5 mm. Width: About 2 mm. Shape: Ovate. Apex: Obtuse to rounded. Base: Truncate. Margin: Grooved. Texture (both surfaces): Glabrous, Silky. Color (Immature and Mature): Apex RHS 45A, red. Base RHS 178B, greyed-red.

Reproductive organs:

*Androecium.*—Stamen: Quantity: Many (about 50 to 70), polyandrous, incurved. Some filaments fused to perianth tube (connate). Length: About 14 mm. Color: RHS N74A, red-purple. Anther: Shape: Ovoid. Length: About 1 mm. Color: RHS 16A, yellow-orange. Filament: Length: About 12 to 13 mm. Color: RHS N74A, red-purple. Pollen: Amount: Abundant. Color: RHS 16A, yellow-orange.

*Gynoecium.*—Pistil: Quantity: 1. Shape: Claw-like. Length: About 19 mm. Stigma: Shape: Ovoid Color: RHS 158C, yellow white. Style: Length: About 16 mm. Color: Base: RHS 158C, yellow-white. Apex: RHS N74C, red-purple. Ovary: Shape: Angular. Length: About 5 mm. Width: About 2 mm to 3 mm. Color: RHS NN155D, white.

Seeds/fruit: None observed.

Disease/pest resistance: No test for disease/pest resistance have been performed yet.

Disease/pest susceptibility: No test for disease/pest resistance have been performed yet.

Temperature tolerance: Tolerant to a low temperature of about 2° C. and to a high temperature about 40° C. Good tolerance to drought.

I claim:

1. A new and distinct *Rhipsalidopsis* plant named 'PKMRH02', as illustrated and described herein.

* * * * *